United States Patent [19]
Deckner

[11] Patent Number: 5,755,789
[45] Date of Patent: May 26, 1998

[54] ARTICULAR PROSTHESIS ASSEMBLED IN STEPS

[76] Inventor: André Georges Deckner, 5 Rue de l'Harmonie 75015, Paris, France

[21] Appl. No.: 792,879

[22] Filed: Jan. 31, 1997

[30] Foreign Application Priority Data

Feb. 8, 1996 [FR] France .................. 96 01539

[51] Int. Cl.$^6$ .................. A61F 2/02; A61F 2/30
[52] U.S. Cl. .................. 623/11; 623/18
[58] Field of Search .................. 623/18, 20, 22, 623/23, 11

[56] References Cited

U.S. PATENT DOCUMENTS 5,405,392  4/1995  Deckner .................. 623/18

FOREIGN PATENT DOCUMENTS 0 681 816  11/1995  European Pat. Off. .
95 13757   5/1995   WIPO .................. A61B 17/86

Primary Examiner—Debra S. Brittingham
Attorney, Agent, or Firm—Pearne, Gordon, McCoy & Granger LLP

[57] ABSTRACT

This articular prosthesis comprises a proximal part (P) and a distal part (D) having a form such that one of these is female and the other male when they are assembled along an impaction axis by their opposite mating faces, each opposite face comprising several stepped sections, each section being in the form of a truncated cone, wherein the thickness (E, e) of consecutive sections of one of the parts increases, while the thickness of the mating consecutive sections of the other part decreases.

8 Claims, 1 Drawing Sheet

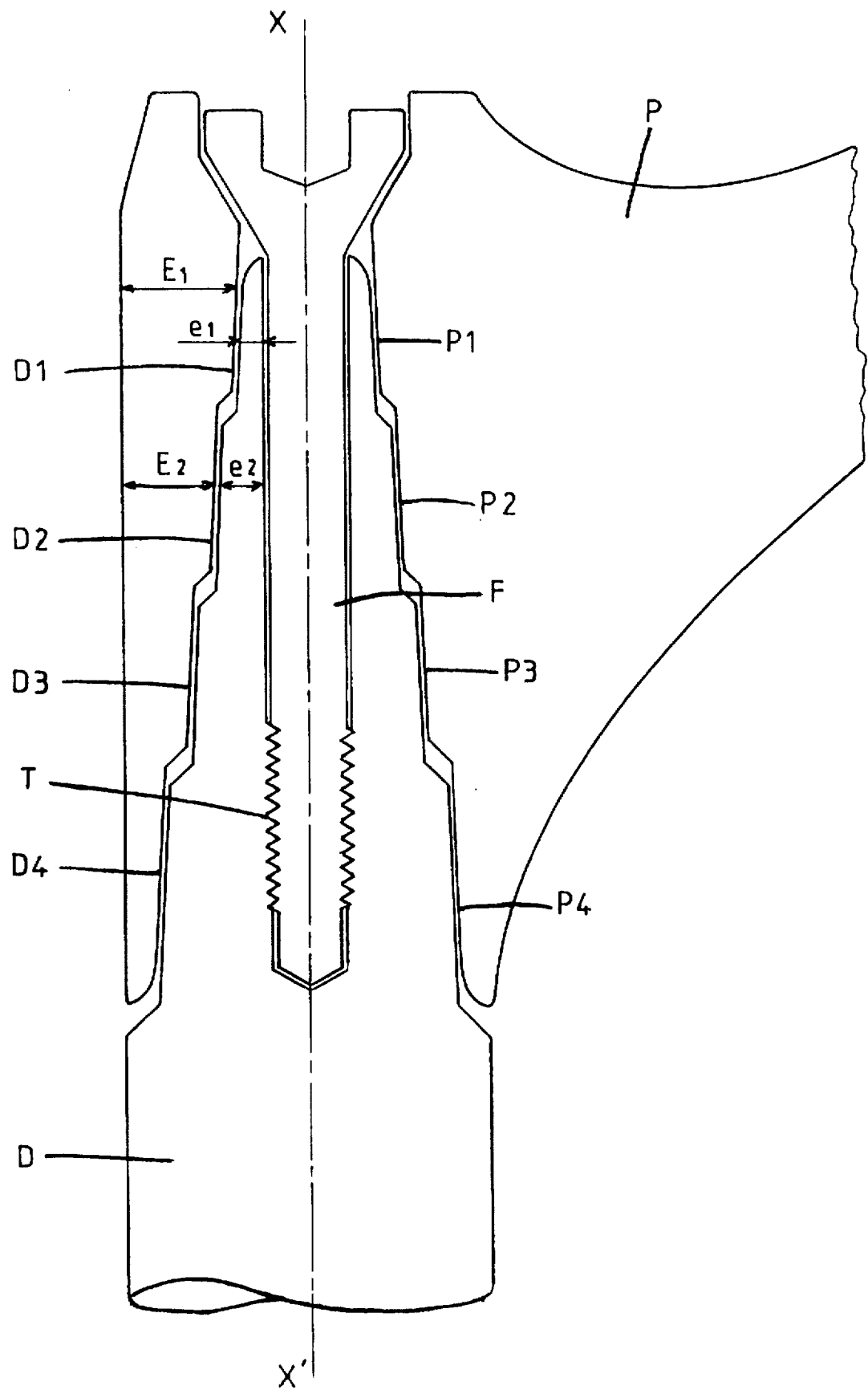

3,755,789

ARTICULAR PROSTHESIS ASSEMBLED IN STEPS

BACKGROUND OF THE INVENTION

The invention relates to surgical implants, in particular articular prostheses intended more particularly for hip prostheses.

An articular prosthesis is already known comprising a proximal part and a distal part. These parts are assembled to each other by a clamping joint. All known joints give rise to micro-movements after a large number of loadings. These micro-movements occur on account of there being too great a difference between the localized stresses in the metal masses in the immediate vicinity and either side of the location of the joint, known hereinafter as the "junction point". Normal joints have very large variations in the cross-section of the two components to be assembled, in the vicinity of the joint. These excessive variations in the cross-section and shape result in large variations in the stresses within the materials when repeated loadings occur. Relative micro-movements occur either side of the said junction point. These micro-movements eventually cause mutual abrasion of the two parts producing wear and giving rise to wear debris.

SUMMARY OF THE INVENTION

The materials constituting the surfaces of the joint and constituting the components to be assembled may each be metallic, ceramic or plastic.

The invention aims at reducing significantly the differences in stresses in the masses in the vicinity of the junction point and aims at retarding the appearance of wear to an appreciable extent. Although both the proximal part and the distal part have a weak portion, the mechanical strength of the joint is improved so that it can withstand stresses caused by the patient walking over several years.

The invention thus concerns an articular prosthesis comprising a proximal part and a distal part having a form such that one of them is female and the other male when they are assembled together along an impaction axis by opposite faces. According to the invention, each opposite face comprises several stepped sections, each section being in the form of a truncated cone, the thickness of consecutive sections of one of the parts increasing, while the thickness of the consecutive sections of the other part decreases.

The thickness is defined by a dimension in a direction perpendicular to the impaction axis, which is coincidental with the direction of assembly.

By virtue of the fact that each opposite face is subdivided into several sections having thicknesses which are calculated independently, each of these sections may be given a sufficiently small taper (angle between the generatrix and the impaction axis), this small angle being necessary for ensuring good attachment of the opposite surfaces by conical assembly. Although the length of the assembly region is of necessity relatively small in an articular prosthesis, the succession of sections enables a progressive transfer to take place of the load applied to the joint from one component to the other, so that the parts which are weak, because they are thinner, no longer support, on their own, loads which are too great and are likely to cause a break. Steps are provided since, contrary to a joint with a single cone having the same angle, the steps do not bring about an unacceptable mechanical weakness for one or both of the parts nor are there sudden variations in thickness of the materials, where excessive stresses in the material are localized in the vicinity of sudden variations in cross-section.

U.S. Pat. No. 5,405,392 does not describe the thickness of consecutive sections of one of the parts as increasing, with the thickness of the consecutive sections of the other part decreasing, nor does the American patent describe the result where, by virtue of this, differences in stresses are reduced in the masses in the vicinity of the junction point and the occurrence of wear is retarded.

Each part comprises a small number of steps (2 to 20) and the axial extent of each step is greater than 1 mm.

The steps do not themselves constitute a surface microstructure or a system of attachment comprising teeth, but each operates as a conical joint, being associated with its own mating section.

Preferably, the angle between the generatrix of each section and the impaction axis $xx'$ is less than 5° and preferably less than 3°.

According to an improvement, the two parts to be assembled are not only impacted in the direction of the axis, but are also subjected to a high tensile force one in the direction of the other along the axis, so that the male part is slightly compressed and the female part is slightly expanded within the limits of the elastic properties peculiar to each material. This constitutes a prestressing of the joint and increases the limit above which relative micro-movements will occur in use.

This prestressing may be obtained, for example, by having a threaded end on the male part onto which a nut is screwed bearing on the female part, or for example by having a threaded rod gripping the female part and supported in a tapped hole in the male part.

The amount of taper of the successive sections of one of the parts may be different, with the aim of deliberately producing a better distribution of stresses along the joint to adapt to different thicknesses of material.

According to an improvement, a section of one of the parts mating with a section of the other part has a different amount of taper from that of the mating section so as to produce a better distribution of stresses between the two ends of the same section.

BRIEF DESCRIPTION OF THE DRAWINGS

The invention is illustrated in the single FIGURE of the accompanying drawing.

The FIGURE is a sectional view of an articular prosthesis according to the invention.

DESCRIPTION OF THE PREFERRED EMBODIMENT

This prosthesis comprises a female proximal part P and a male distal part D entering the proximal part P. The part P comprises, for this purpose, a central bore having four stepped sections, P1, P2, P3 and P4, the thickness E2 of the step P2 being less than the thickness E1 of the step P1 and similarly thereafter as a function of the steps.

The distal part D also comprises 4 steps D1, D2, D3 and D4, mating with the steps P1, P2, P3 and P4. The thickness e1 of the step D1 is this time less than the thickness e2 of the step D2 and similarly thereafter for the steps D3 and D4. Each section P1, P4 and its mating section D1, D4 is in the form of a truncated cone making an angle of approximately 4° with the impaction axis $xx'$.

The distal part D comprises a tapping T having the same axis as the impaction axis $xx'$, into which is screwed a threaded rod F which has been prestressed axially.

I claim:

1. Articular prosthesis comprising a proximal part and a distal part having a form such that one part is female and has a female mating face, and the other part is male and has a male mating face adapted to be disposed opposite said female mating face when said parts are assembled along an impaction axis, each opposite face comprising several stepped sections consecutively disposed along said axis when said parts are assembled, each section being in the form of a truncated cone and having a thickness wherein the thicknesses of all consecutive sections of one of the parts increases, while the thicknesses of all the mating consecutive sections of the other part decreases.

2. Prosthesis according to claim 1, wherein the angle between the generator of each section and the impaction axis is less than 5°.

3. Prosthesis according to claim 1, comprising means for axially prestressing the parts.

4. Prosthesis according to claim 3, wherein one of the two parts comprises a tapping having an axis coincident with the impaction axis, into which is screwed a threaded rod which has been axially prestressed.

5. Prosthesis according to claim 1, wherein the successive sections of one of the parts have different tapers.

6. Prosthesis according to claim 1, wherein the angle between the generator of each section and the impaction axis is less than 3°.

7. Prosthesis according to claim 1, wherein a pair of associated sections of said parts includes first and second sections having different tapers with respect to said impaction axis.

8. A method for modifying the distribution of stresses in a prosthesis having a construction in accordance with clain 1, including forming a pair of associated sections having axially spaced section ends and different tapers relative to said impaction axis to thereby modify the distribution of stresses between said section ends.

* * * * *